United States Patent
Choi et al.

(10) Patent No.: US 9,936,889 B2
(45) Date of Patent: Apr. 10, 2018

(54) APPARATUS AND METHOD OF CONTROLLING THRESHOLD FOR DETECTING PEAKS OF PHYSIOLOGICAL SIGNALS

(71) Applicant: Samsung Electronics Co., Ltd., Suwon-si (KR)

(72) Inventors: Chang-mok Choi, Seoul (KR); Youn-ho Kim, Hwaseong-si (KR); Kun-soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 163 days.

(21) Appl. No.: 13/782,483

(22) Filed: Mar. 1, 2013

(65) Prior Publication Data
US 2013/0237868 A1    Sep. 12, 2013

(30) Foreign Application Priority Data

Mar. 8, 2012    (KR) .................. 10-2012-0024114
Mar. 13, 2012    (KR) .................. 10-2012-0025667

(51) Int. Cl.
*A61B 5/04*       (2006.01)
*A61B 5/0456*     (2006.01)
*A61B 5/00*       (2006.01)

(52) U.S. Cl.
CPC ...... *A61B 5/04014* (2013.01); *A61B 5/04012* (2013.01); *A61B 5/0456* (2013.01); *A61B 5/7239* (2013.01); *A61B 5/746* (2013.01)

(58) Field of Classification Search
CPC ........... A61B 5/01; A61B 5/02; A61B 5/0205; A61B 5/04; A61B 5/0456; A61B 5/72; A61B 5/7271; A61B 5/7275

USPC ......................................................... 600/509
See application file for complete search history.

(56) References Cited

U.S. PATENT DOCUMENTS 5,318,036 A    6/1994    Arand et al.
5,339,820 A    8/1994    Henry et al.
(Continued)

FOREIGN PATENT DOCUMENTS

JP    61-45734 A    3/1986
JP    6-14896 A    1/1994
(Continued)

OTHER PUBLICATIONS

Pan, Jiapu, et al. "A Real-Time QRS Detection Algorithm." *IEEE Transactions on Biomedical Engineering*, vol. 32, No. 3 (1985): 230-236.
(Continued)

*Primary Examiner* — Michael Carey
*Assistant Examiner* — Elizabeth K So
(74) *Attorney, Agent, or Firm* — NSIP Law

(57) ABSTRACT

A method of controlling a threshold for detecting peaks of physiological signals includes: obtaining a physiological signal measured from a person being examined; determining whether a peak of the physiological signals is detected based on a result of comparing the physiological signals with a threshold; and controlling the threshold based on a minimum threshold and either the threshold or a feature value of the detected peak based on a result of the determining. When a threshold for detecting peaks of physiological signals is controlled, even if an interval between the peaks is irregular or there is a large difference in values of the peaks, the peaks can be accurately detected.

9 Claims, 9 Drawing Sheets

(56) References Cited

U.S. PATENT DOCUMENTS

| | | | |
|---|---|---|---|
| 5,891,048 | A | 4/1999 | Nigam et al. |
| 6,547,746 | B1* | 4/2003 | Marino .................... 600/554 |
| 7,149,331 | B1 | 12/2006 | Kaufman et al. |
| 8,475,388 | B2* | 7/2013 | Ni et al. .................... 600/529 |
| 2009/0264956 | A1* | 10/2009 | Rise .................... A61B 5/4836 607/45 |
| 2010/0168594 | A1 | 7/2010 | Chuang |
| 2011/0015468 | A1 | 1/2011 | Aarts et al. |

FOREIGN PATENT DOCUMENTS

| | | |
|---|---|---|
| JP | 2820721 B2 | 8/1998 |
| JP | 2001-70265 A | 3/2001 |
| KR | 10-1029386 B1 | 4/2011 |
| WO | WO 00/04824 A1 | 2/2000 |

OTHER PUBLICATIONS

Tabakov, Serafim, et al. "Online Digital Filter and QRS Detector Applicable in Low Resource ECG Monitoring Systems." *Annals of Biomedical Engineering* vol. 36, No. 11 (2008): 1805-1815.

Lin, Chin-Teng, et al. "An Intelligent Telecardiology System Using a Wearable and Wireless ECG to Detect Atrial Fibrillation." *IEEE Transactions on Information Technology in Biomedicine*, vol. 14, No. 3 (2010): 726-733.

Chinese Office Action dated Mar. 25, 2016 in counterpart Chinese Application No. 201310067856.6 (14 pages in Chinese with English translation).

Japanese Office Action dated Feb. 28, 2017 in corresponding Japanese Patent Application No. 2013-045910 (4 pages in English and 2 Pages in Japanese.

* cited by examiner

APPARATUS AND METHOD OF CONTROLLING THRESHOLD FOR DETECTING PEAKS OF PHYSIOLOGICAL SIGNALS

CROSS-REFERENCE TO RELATED APPLICATIONS

This application claims the benefit of Korean Patent Application Nos. 10-2012-0024114 filed on Mar. 8, 2012, and 10-2012-0025667 filed on Mar. 13, 2012, in the Korean Intellectual Property Office, the disclosures of which are incorporated herein by reference in their entirety for all purposes.

BACKGROUND

1. Field

This application relates to methods and apparatuses for detecting physiological signals of persons to be examined.

2. Description of Related Art

Various methods of measuring and analyzing physiological signals used to diagnose patients have been used or developed. As interest in medical services for providing health management and chronic disease management in real time in everyday life by measuring physiological signals of persons to be examined increases, the importance of methods of measuring and analyzing physiological signals more precisely has been emphasized.

Among these physiological signals, electrocardiography (ECG) involves attaching electrodes to a human body and measuring action potentials that occur when a heart muscle contracts. Methods of measuring and analyzing ECG signals in order to examine the function of the heart and in order to diagnose various diseases have been widely used.

In order to calculate heart rates or in order to diagnose the occurrence of arrhythmia by analyzing ECG signals, a single P-Q-R-S-T waveform that occurs when the heart contracts once must first be detected. By detecting a single waveform, heart rates can be calculated by calculating an interval between waveforms, and by extracting a single waveform, arrhythmia can be diagnosed based on a shape of the single waveform. A method of detecting an R-waveform having the greatest size in the single P-Q-R-S-T waveform is usually used to detect the single waveform.

SUMMARY

In one general aspect, a method of controlling a threshold for detecting peaks of physiological signals includes obtaining a physiological signal measured from a person being examined; determining whether a peak of the physiological signal is detected based on a result of comparing the physiological signal with a threshold; and controlling the threshold based on a minimum threshold and either the threshold or a feature value of the detected peak based on a result of the determining.

The minimum threshold may be a value to which the threshold converges as the threshold is updated as a result of the controlling.

The minimum threshold may be predetermined based on a range of values of the physiological signal that can be measured by a sensor configured to measure the physiological signal of the person to be examined.

The minimum threshold may vary in real time based on a value of the physiological signal.

The minimum threshold may vary in real time based on a feature value of the physiological signal.

The controlling may include controlling the threshold based on the feature value of the detected peak and a value obtained by applying a predetermined weight to a difference between the feature value of the detected peak and the minimum threshold when the result of the determining is that a peak of the physiological signal is detected.

The controlling may include controlling the threshold based on the threshold and a value obtained by applying a predetermined weight to a difference between the threshold and the minimum threshold when the result of the determining is that a peak of the physiological signal is not detected.

The controlling may include controlling the threshold based on the threshold and a previous threshold that was updated to obtain the threshold.

The controlling may include controlling the threshold based on a value obtained by applying a predetermined weight to a difference between the feature value of the detected peak and a previous threshold that was updated to obtain the threshold when a result of the determining is that a peak of the physiological signal is detected.

The controlling may include controlling the threshold based on a value obtained by applying a predetermined weight to a difference between the threshold and a previous threshold that was updated to obtain the threshold when a result of the determining is that a peak of the physiological signal is not detected.

In another general aspect, an apparatus for controlling a threshold for detecting peaks of physiological signals includes a signal obtaining unit configured to obtain a physiological signal measured from a person to be examined; a determining unit configured to determine whether a peak of the physiological signal is detected based on a result of comparing the physiological signal with a threshold; and a controlling unit configured to control the threshold based on a minimum threshold and either the threshold or a feature value of the detected peak based on a result obtained by the determining unit.

The minimum threshold may be a value to which the threshold converges as the threshold is updated as a result of the control performed by the controlling unit.

The minimum threshold may vary in real time based on a feature value of the physiological signal.

The controlling unit may be further configured to control the threshold based on the feature value of the detected peak and a value obtained by applying a predetermined weight to a difference between the feature value of the detected peak and the minimum threshold when the result obtained by the determining unit is that a peak of the physiological signal is detected.

The controlling unit may be further configured to control the threshold based on the threshold and a value obtained by applying a predetermined weight to a difference between the threshold and the minimum threshold when the result obtained by the determining unit is that a peak of the physiological signal is not detected.

The controlling unit may be further configured to control the threshold based on the threshold and a previous threshold that was updated to obtain the threshold.

The controlling unit may be further configured to control the threshold based on a value obtained by applying a predetermined weight to a difference between the feature value of the detected peak and a previous threshold that was updated to obtain the threshold when the result obtained by the determining unit is that a peak of the physiological signal is detected.

The controlling unit may be further configured to control the threshold based on a value obtained by applying a predetermined weight to a difference between the threshold and a previous threshold that was updated to obtain the threshold when the result obtained by the determining unit is that a peak of the physiological signal is not detected.

In another general aspect, a non-transitory computer-readable storage medium stores a program for controlling a computer to perform a method of controlling a threshold for detecting peaks of physiological that includes obtaining a physiological signal measured from a person being examined; determining whether a peak of the physiological signal is detected based on a result of comparing the physiological signal with a threshold; and controlling the threshold based on a minimum threshold and either the threshold or a feature value of the detected peak based on a result of the determining.

In another general aspect, an apparatus for detecting physiological signals includes electrodes configured to be attached to a person to be examined to measure a physiological signal from the person to be examined; a processing unit configured to process the measured physiological signal using a predetermined processing method to obtain a processed physiological signal; a determining unit configured to determine whether a peak of the physiological signal is detected based on a result of comparing the processed physiological signal with a threshold; and a threshold controlling unit configured to control the threshold based on a minimum threshold and either the threshold or a feature value of the detected peak based on a result obtained by the determining unit.

Other features and aspects will be apparent from the following detailed description, the drawings, and the claims.

DETAILED DESCRIPTION

Figure 1:
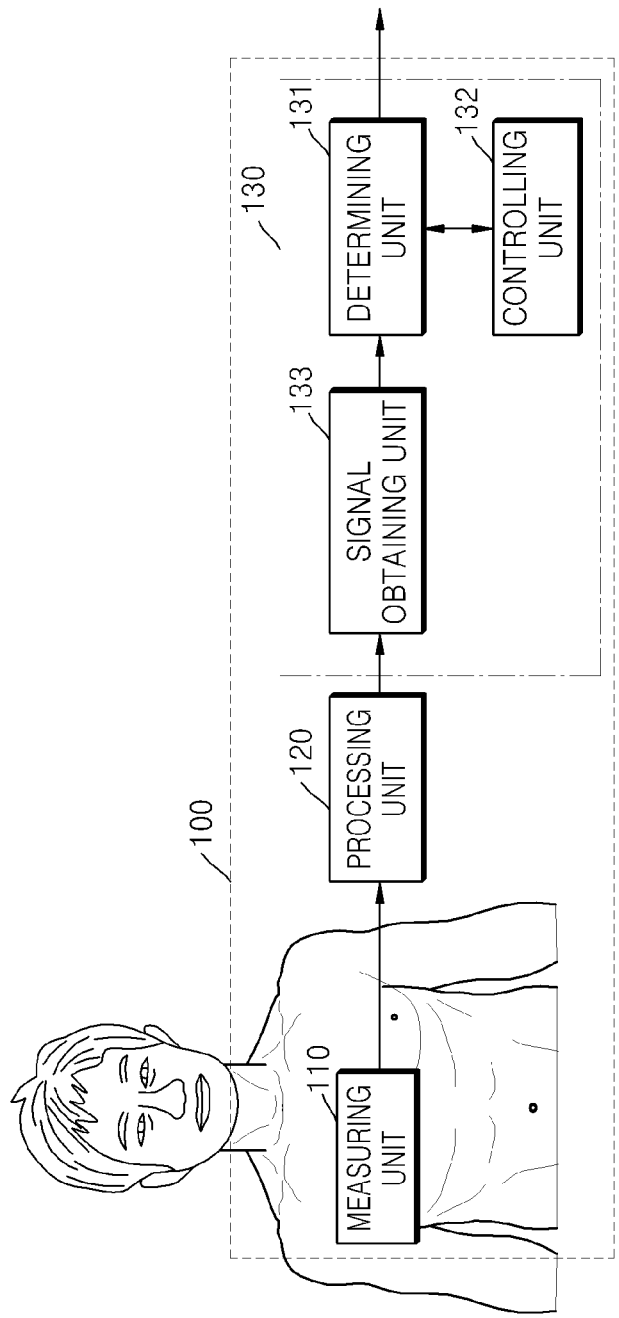
FIG. 1 illustrates an example of an apparatus for detecting physiological signals.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 illustrates an example of an apparatus 100 for detecting physiological signals. Referring to FIG. 1, the apparatus 100 for detecting physiological signals includes a measuring unit 110, a processing unit 120, and a threshold controlling unit 130. The threshold controlling unit 130 includes a determining unit 131, a controlling unit 132, and a signal obtaining unit 133. The apparatus 100 for detecting physiological signals illustrated in FIG. 1 is just one example, and it will be understood by one of ordinary skill in the art that elements of the apparatus 100 for detecting physiological signals of FIG. 1 may be modified in various ways.

The apparatus 100 for detecting physiological signals of FIG. 1 measures physiological signals of a person to be examined and analyzes the measured physiological signals, thereby detecting necessary information.

The physiological signals may be potential signals or current signals that are generated in muscle cells or nerve cells of a human body. Hereinafter, for convenience of explanation, the physiological signals to be detected using the apparatus 100 for detecting physiological signals will be considered to be potential signals. However, it will be understood by one of ordinary skill in the art based on the following description that various examples may be applied to various physiological signals.

In addition, when describing this example, electrocardiography (ECG) signals will be described as an example of physiological signals. However, it will be understood by one of ordinary skill in the art based on the following description that various examples may be applied to various physiological signals. ECG signals will be described with reference to FIG. 3.

The measuring unit 110 is attached to the body of the person to be examined and measures physiological signals of the person to be examined. For example, the measuring unit 110 is placed in contact with the skin of the person to be examined, is electrically connected to the skin of the person to be examined, and measures physiological signals of the person to be examined. The measuring unit 110 may be one or more electrodes that electrically contact the person to be examined, so that electrical signals can be transmitted or received between the person to be examined and a circuit for measuring physiological signals. One or more electrodes may be arranged in various ways and may contact the skin of the person to be examined in order to detect the physiological signals precisely. However, the measuring unit 110 is not limited to be in contact with the skin of the person to be examined and to be electrically connected to the skin of the person to be examined, and it will be understood by one of ordinary skill in the art that electrical signals can be transmitted or received between the person to be examined and the circuit for measuring physiological signals without contacting the skin of the person to be examined, for example, by being close to the skin of the person to be examined.

For example, the measuring unit 110 may measure physiological signals by measuring a difference in potential values, i.e., a voltage, detected from each of two electrodes attached to a plate spaced apart from the skin of the person to be examined by a predetermined distance. In addition, the measuring unit 110 may measure physiological signals by differentially amplifying potential values obtained from two electrodes attached to a plate spaced apart from the skin of the person to be examined by a predetermined distance using a differential amplifier to obtain waveforms of voltage values corresponding to the physiological signals. The obtained waveforms of the voltage values of the physiological signals may include noise.

The physiological signals corresponding to signals generated in cells are electrical signals having very small amplitudes and are greatly affected by noise. For example, when the physiological signals are measured using the electrodes of the measuring unit 110, undesirable noise may be included in the waveforms of the voltage values of the physiological signals due to an external cause, such as contact with the electrodes, or other external causes. This noise decreases accuracy of the physiological signals and makes it difficult to detect and analyze the physiological signals.

Thus, the processing unit 120 of FIG. 1 processes the physiological signals measured by the measuring unit 110 using a predetermined processing method and transmits the processed physiological signals to the determining unit 131. For example, the processing unit 120 pre-processes ECG signals by applying a band-pass filter to ECG signals measured by the measuring unit 110, and applying a differentiator and a low-pass filter to the band-pass filtered ECG signals, thereby obtaining a feature value representing a feature of the physiological signals. As an example, the low-pass filter may be an absolute moving average filter.

The feature value may be a value representing a feature of the physiological signals processed by the processing method for extracting features of the physiological signals using the processing unit 120. Hereinafter, examples of processing physiological signals using a predetermined processing method in order to obtain a feature value will be described.

Before the band-pass filter is applied to the ECG signals, baseline wandering wherein the entire ECG signals move due to a change in an isoelectric line that is the baseline voltage of the ECG signals, and radio-frequency wandering, such as an electromyogram (EMG), may exist in the ECG signals. Thus, the processing unit 120 may allow signals to be detected to pass through only a frequency band by applying the band-pass filter to the ECG signals in order to prevent baseline wandering and radio-frequency wandering.

When the differentiator is applied to the band-pass filtered ECG signals, an inclination of a single waveform of the ECG signals is steeply changed in the vicinity of an R-waveform. Thus, differential values of the ECG signals in the vicinity of the R-waveform vary rapidly, and the apparatus 100 for detecting physiological signals may detect the R-waveform from the differentiated ECG signals. The R-waveform will be described with reference to FIG. 3 in greater detail.

When the low-pass filter, for example, an absolute moving average filter, is applied to the differentiated ECG signals, the ECG signals include undesirable noise input from the outside while the physiological signals are being obtained. In order to reduce the effect of noise, the processing unit 120 applies the low-pass filter to the ECG signals. An absolute moving average filter may be used as the low-pass filter. The absolute moving average filter is a kind of low-pass filter for obtaining an envelope of a signal waveform and outputs an average value of absolute values of a predetermined number of signals based on the latest signal in order to prevent a rapid variation caused by noise.

It will be understood by one of ordinary skill in the art that the processing unit 120 may process physiological signals using various processing methods other than the above-described processing method.

The threshold controlling unit 130 of FIG. 1 includes the signal obtaining unit 133, the determining unit 131, and the controlling unit 132. The signal obtaining unit 133 obtains physiological signals measured from the person to be examined, or physiological signals processed by the processing unit 120. The determining unit 131 determines whether peaks of the physiological signals are detected based on a result of comparing the obtained physiological signals with a threshold for detecting the peaks of the physiological signals, and the controlling unit 132 controls the threshold based on a minimum value of the threshold and either the threshold or a feature value of the detected peaks based on a determination result of the determining unit 131.

When the feature value of the ECG signals measured from the person to be examined obtained by the signal obtaining unit 133 exceeds the threshold, the determining unit 131 of FIG. 1 determines that the R-waveform is detected.

The controlling unit 132 of FIG. 1 controls a variable threshold. In this case, the variable threshold is not a predetermined constant threshold, but is a variable threshold that varies from a first threshold to a second threshold based on the determination result of the determining unit 131. Hereinafter, an example of a method of controlling the variable threshold using the threshold controlling unit 130 will be described with reference to FIG. 2 in greater detail.

The first threshold is a current threshold, and the second threshold is a threshold to be updated depending on whether peaks are detected by the controlling unit 230. However, the first threshold may also be a threshold updated by the controlling unit 230 from the previous threshold.

Figure 2:
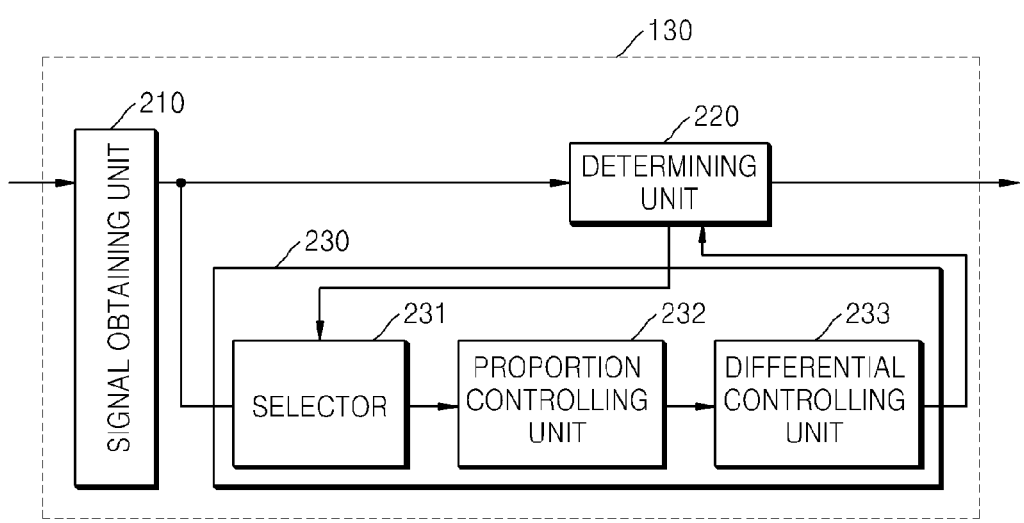
FIG. 2 illustrates an example of a structure of a threshold controlling unit of the apparatus for detecting physiological signals illustrated in FIG. 1.

FIG. 2 illustrates an example of a structure of a threshold controlling unit of the apparatus for detecting physiological signals illustrated in FIG. 1. Referring to FIG. 2, the threshold controlling unit 130 of FIG. 1 includes a signal obtaining unit 210, a determining unit 220, and a controlling unit 230. The controlling unit 230 includes a selector 231, a proportion controlling unit 232, and a differential controlling unit 233.

The signal obtaining unit 210 obtains physiological signals measured from the person to be examined or physiological signals processed by the processing unit 120.

The determining unit 220 determines whether peaks of the physiological signals are detected based on a result of comparing the physiological signals obtained by the signal obtaining unit 210 with a threshold for detecting peaks of physiological signals. For example, the determining unit 220 may compare the physiological signals obtained by the signal obtaining unit 210 with the threshold and may recognize that peaks of the R-waveform are detected if a value of the physiological signals exceeds the threshold based on the comparison result.

The controlling unit 230 controls the threshold by updating the threshold based on a minimum value of the threshold and either the threshold or a feature value of the detected peaks based on the determination result of the determining unit 220. The controlling unit 230 includes a selector 231, a proportion controlling unit 232, and a differential controlling unit 233.

The selector 231 selects either the threshold or the feature value of the detected peaks based on the determination of the determining unit 220. For example, the selector 231 may select the feature value of the detected peaks if it is determined that the peaks of the physiological signals are detected based on determination of the determining unit 220, and may select the threshold if it is determined that the peaks of the physiological signals are not detected.

The proportion controlling unit 232 reduces a value selected by the selector 231 by a predetermined ratio. The proportion controlling unit 232 may adjust a degree by which a variable threshold is based on a predetermined weight and a minimum threshold. Thus, the proportion controlling unit 232 may adjust the variable threshold to always have a larger value than the minimum threshold.

The weight is a ratio for reducing a selected value and may be a rational number that is equal to or greater than 0. The minimum threshold is a lower limit value set so that the variable threshold will not to be reduced to less than a predetermined value even though the minimum threshold varies. The minimum threshold may be a rational number that is greater than 0.

For example, if it is determined that the peaks of the physiological signals are detected based on the determination of the determining unit 220, the proportion controlling unit 233 may control the threshold by setting the threshold to a value obtained by subtracting a value obtained by applying a predetermined weight to a difference between the feature value of the peaks of the physiological signals and the minimum threshold from the feature value of the peaks of the physiological signals.

Alternatively, if it is determined that the peaks of the physiological signals are not detected based on the determination of the determining unit 220, the proportion controlling unit 232 may control the threshold by setting the threshold to a value obtained by subtracting a value obtained by applying a predetermined weight to a difference between the threshold and the minimum threshold from the threshold.

Thus, the proportion controlling unit 232 may reduce the value selected by the selector 231 by a predetermined ratio by performing an arithmetic operation according to the following Equation 1:

$$TH(t)=TH(t-1)-a(TH(t-1)-TH_{min}) \quad (1)$$

In Equation 1, TH(t) is a second threshold updated as the value selected by the selector 231 is reduced by a predetermined ratio by the proportion controlling unit 232, TH(t−1) is one value selected by the selector 231 from a first threshold and a feature value of the physiological signals, a is a weight indicating a degree by which a variable threshold is reduced, and $TH_{min}$ is a minimum threshold.

The weight a may be a rational number that is equal to or greater than 0, and may be properly adjusted by a user of the threshold controlling unit 130 based on a user environment. For example, the weight a may be properly adjusted by the user of the threshold controlling unit 130 based on a type of physiological signals to be detected, the length of a single waveform, or other factors.

For example, the proportion controlling unit 232 may increase a speed at which the variable threshold is reduced by increasing the weight a. Alternatively, the proportion controlling unit 232 may decrease the speed at which the variable threshold is reduced by decreasing the weight a.

In addition, the minimum threshold $TH_{min}$ may be properly set by the user of the threshold controlling unit 130, and may be preset as a rational number that is greater than 0, or may be properly adjusted based on the user environment.

For example, the minimum threshold may be preset based on a feature value of peaks to be detected from the obtained physiological signals. In the obtained physiological signals, when the feature value of the peaks is higher than a predetermined lower limit value and undesirable noise is lower than a predetermined upper limit value, the lower limit value of the feature value and the upper limit value of noise may be obtained previously, and a minimum threshold may be set to an intermediate value between the obtained lower limit value of the feature value and the obtained upper limit value of noise. The set minimum threshold becomes a lower limit value of a variable threshold.

As described above, since the determining unit 220 recognizes that the peaks are detected when the feature value of the physiological signals exceeds a threshold, as the minimum threshold is set, the determining unit 220 does not recognize the feature value of the physiological signals that has a shape of a peak but is smaller than the minimum threshold as a peak. Thus, the user of the threshold controlling unit 130 may adjust the minimum threshold properly and may ignore a signal having a magnitude that may be regarded as ignorable noise among the feature values of the physiological signals transmitted from the signal obtaining unit 210.

Alternatively, the minimum threshold may be set based on a range where the physiological signals of the person to be examined may be measured by a sensor for measuring the physiological signals of the person to be examined. For example, the minimum threshold may be set by performing an arithmetic operation according to the following Equation 2:

$$TH_{min}=C(S_{max}-S_{min}) \quad (2)$$

In Equation 2, $TH_{min}$ is a minimum threshold, c is a constant, $S_{max}$ is a maximum value that can be measured by a sensor, and $S_{min}$ is a minimum value that can be measured by the sensor. That is, the minimum threshold may be set using Equation 2 so that a value corresponding to a predetermined ratio in the range of values that can be measured by the sensor cannot be recognized as a peak.

For example, when a maximum value of signals that can be measured by the sensor is 100 and a minimum value thereof is −100, if the constant c is set to 0.1, a minimum threshold is 20. By setting the minimum threshold in this way, the variable threshold varies in a range greater than 20. Thus, physiological signals having a value smaller than 20 are not detected as peaks and are ignored.

Alternatively, the minimum value may be preset as a constant as described above, and may be set to vary in real time based on the size of a peak value detected in real time, the magnitude of a signal that is not detected as a peak value among physiological signals, the size of a feature value of a peak value detected in real time, and the size of a feature value of a signal that is not detected as a peak value among physiological signals. For example, a minimum threshold that varies in real time may be set by performing an arithmetic operation according to the following Equation 3:

$$TH_{min} = d(V(t)) \quad (3)$$

In Equation 3, $TH_{min}$ is a minimum threshold, d is a constant, and V(t) may be a just-previously-detected peak value or an average value of a plurality of the latest-detected peak values depending on the circumstances. In this case, the constant d may be properly set as a rational number that is greater than 0 so that peaks having larger values than the minimum threshold can be detected.

Alternatively, V(t) may be a value of physiological signals that are not detected as a just-previously-detected peak value immediately or an average value of a plurality of values of physiological signals that are not the latest-detected peak values depending on circumstances. In this case, the constant d may be properly set as a rational number that is greater than 0 so that a larger peak value than the minimum threshold can be detected.

Alternatively, V(t) may be a feature value detected immediately before or an average value of feature values corresponding to a plurality of peaks detected latest depending on the circumstances. In this case, the constant d may be set to be smaller than 1 so that a larger peak value than the minimum threshold can be detected.

Alternatively, V(t) may be a feature value that is not detected as a just-previously-detected peak or an average value of a plurality of feature values that are not the latest-detected peaks depending on the circumstances. In this case, the constant d may be set to be larger than 1 so that a larger peak value than the minimum threshold can be detected.

However, the above-described methods are just one example for setting a minimum value, and it will be understood by one of ordinary skill in the art that a minimum value that varies in real time can be set using other methods, if necessary. Examples in which a threshold is reduced by control performed by the proportion controlling unit 232 will be described with reference to FIG. 5.

The differential controlling unit 233 may reduce the threshold reduced by the proportion controlling unit 232 once again. The differential controlling unit 233 may adjust a degree by which a variable threshold is reduced by applying a weight to a difference between either a first threshold or a feature value of physiological signals selected by the selector 231 and a previous threshold. In this case, the previous threshold is a threshold before the variable threshold was updated to obtain the first threshold.

For example, when peaks of physiological signals are detected based on the determination of the determining unit 220, the differential controlling unit 233 may control the threshold by reducing a value obtained by applying a predetermined weight to the difference between the feature value of the peaks of the physiological signals and the previous threshold from the feature value of the peaks of the physiological signals.

Thus, the proportion controlling unit 232 and the differential controlling unit 233 may reduce the value selected by the selector 231 by a predetermined ratio by performing an arithmetic operation according to the following Equation 4:

$$TH(t) = TH(t-1) - a(TH(t-1) - TH_{min}) - b(TH(t-1) - TH(t-2)) \quad (4)$$

In Equation 4, TH(t) is a second threshold reduced and updated by the differential controlling unit 233, TH(t−1) is either a first threshold or a feature value of physiological signals selected by the selector 231, a is a weight indicating a degree by which a variable threshold is reduced by the proportion controlling unit 232, $TH_{min}$ is a minimum threshold, b is a weight indicating a degree by which the variable threshold is reduced by the differential controlling unit 233, and TH(t−2) is the previous threshold that is a threshold before being updated to obtain the first threshold. The differential controlling unit 233 prevents a rapid variation of the variable threshold by reducing the variable threshold again in proportion to the amount of the variation of the variable threshold.

For example, if it is determined that the peaks of the physiological signals are detected by the determining unit 220, the selector 231 selects the feature value of the peaks of the physiological signals as TH(t−1), and the proportion controlling unit 232 subtracts a value obtained by applying the weight a to a difference between the feature value of the peaks of the physiological signals and the minimum threshold from the feature value of the peaks of the physiological signals, and the differential controlling unit 233 further subtracts a value obtained by applying the weight b to a difference between the feature value of the peaks of the physiological signals and the previous threshold from the result obtained by the proportion controlling unit 232 to obtain the second threshold as an updated threshold.

On the other hand, if it is determined that the peaks of the physiological signals are not detected by the determining unit 220, the selector 231 selects the first threshold as TH(t−1), and the differential controlling unit 232 subtracts a value obtained by applying the weight a to a difference between the first threshold and the minimum threshold from the first threshold, and the differential controlling unit 233 further subtracts a value obtained by applying the weight b to a difference between the first threshold and the previous threshold from the result obtained by the proportion controlling unit 232 to obtain the second threshold as an updated threshold.

In this case, if the peaks of the physiological signals are not detected, the threshold is updated to a smaller value. Thus, a value of TH(t−1)−TH(t−2) is smaller than 0, and if b is greater than 0, the differential controlling unit 233 increases the threshold using Equation 4.

That is, the differential controlling unit 233 may be a kind of low-pass filter that prevents a rapid variation of the variable threshold since the variable threshold is further controlled in proportion to the amount of variation of the variable threshold. This will be described in greater detail with reference to FIGS. 6A and 6B.

The weight b in this example may be any rational number, and may be appropriately adjusted by the user of the threshold controlling unit 130 based on circumstances of use. For example, the weight b may be properly adjusted by the user of the threshold controlling unit 130 based on a type of physiological signals to be detected, a variation pattern of a feature value, or other factors.

For example, the differential controlling unit 233 may be further affected by the amount of variation of the variable threshold by increasing the weight b. Alternatively, the differential controlling unit 233 may be less affected by the amount of variation of the variable threshold by decreasing the weight b. This will be described with reference to FIGS. 6A and 6B in greater detail.

As described above, the threshold controlling unit 130 of FIG. 2 may control the threshold so that the peaks of the physiological signals can be detected even when an interval between the peaks is not uniform or a feature value of the peaks are not uniform by controlling the variable threshold using the threshold controlling unit 132.

Figure 3:
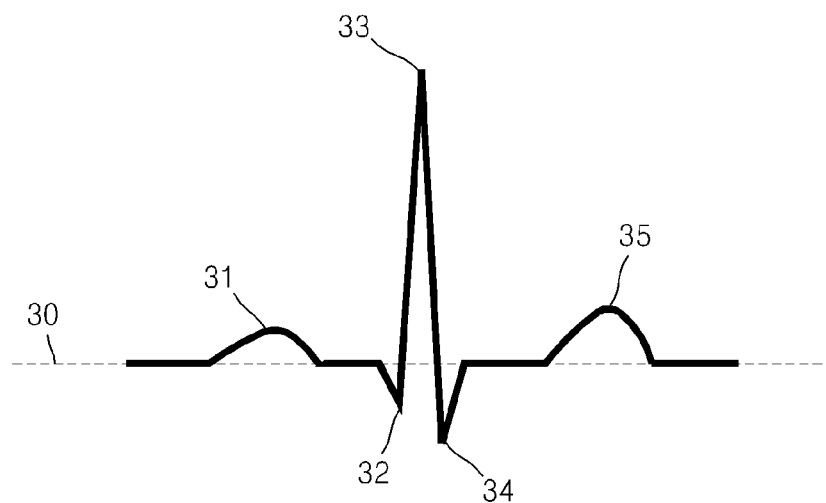
FIG. 3 illustrates an example of a single waveform of electrocardiography (ECG) signals as an example of physiological signals.

FIG. 3 illustrates an example of a single waveform of ECG signals as an example of physiological signals. Performing an ECG involves attaching electrodes to a human body and measuring action potentials that occur when a heart muscle contracts. Methods of measuring and analyzing ECG signals in order to inspect the function of the heart and in order to diagnose various diseases have been widely used, and accordingly will not be discussed in detail here for conciseness.

Referring to FIG. 3, five peaks that protrude from an isoelectric line 30 exist in a single waveform of ECG signals, wherein the peaks are referred to as P (31), Q (32), R (33), S (34), and T (35) waveforms. Whenever the heart contracts once, one single waveform occurs. The apparatus 100 for detecting physiological signals in this example may detect an R-waveform having the largest size in a single P-Q-R-S-T waveform in order to detect the single waveform of the ECG signals.

By detecting a single waveform, a computer or a medical expert may calculate heart rates by calculating an interval between waveforms and may diagnose arrhythmia based on a shape of the detected single waveform.

The variable threshold discussed above will be described with reference to FIG. 4 in detail.

Figure 4:
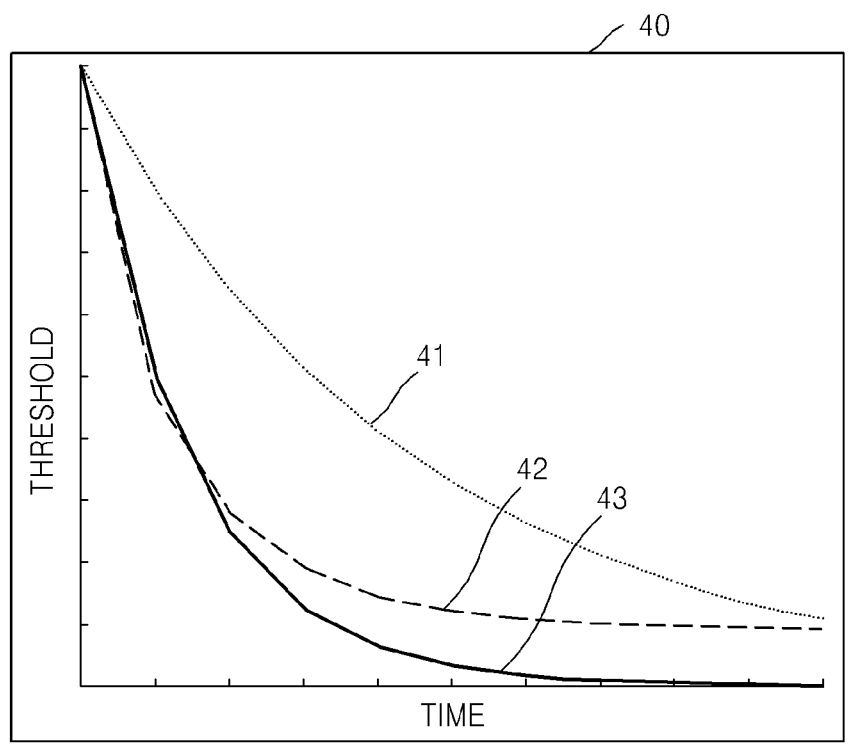
FIG. 4 is a graph illustrating an example of a variable threshold for detecting physiological signals that is controlled over time.

FIG. 4 is a graph illustrating an example of a variable threshold for detecting physiological signals that is controlled over time. Referring to FIG. 4, the variable threshold for detecting an R-waveform of ECG signals is controlled so that when the R-waveform is detected, a value of the variable threshold is updated based on a feature value of the R-waveform, and is gradually reduced until a new R-waveform is detected. An example of controlling the variable threshold will be explained using graphs 41, 42, and 43 in FIG. 4.

Referring to FIG. 4, when the variable threshold is controlled in the shape of graph 41, after the R-waveform is detected, a speed at which the value of the variable threshold is reduced is relatively slow compared to graphs 42 and 43. Thus, when an interval between R-waveforms is short, if a new R-waveform occurs in a state where the variable threshold has not been sufficiently reduced, the value of the R-waveform does not exceed the variable threshold, preventing the determining unit 131 from detecting a new R-waveform.

When the variable threshold is controlled in the shape of graph 43, after the R-waveform is detected, a speed at which the value of the variable threshold is reduced is relatively fast compared to graph 41. Thus, even when an interval between R-waveforms is short, the variable threshold is sufficiently quickly reduced. Thus, if a new R-waveform occurs, the value of the R-waveform exceeds the variable threshold, enabling the determining unit 131 to detect a new R-waveform. However, if the variable threshold is reduced too quickly and gradually converges to a value of 0 as shown in graph 43, a very small noise that exists in the vicinity of 0 may exceed the variable threshold so that the determining unit 131 may incorrectly detect the noise as an R-waveform. Even when an interval between R-waveforms is very long, the variable threshold still gradually converges to a value of 0 so that the same problem may occur.

On the other hand, when the variable threshold is controlled in the shape of graph 42, after an R-waveform is detected like when being controlled in the shape of graph 43, the speed at which the variable threshold is reduced is relatively fast and the variable threshold gradually converges to a minimum threshold greater than 0 so that the variable threshold does not converge to the value of 0.

Figure 5:
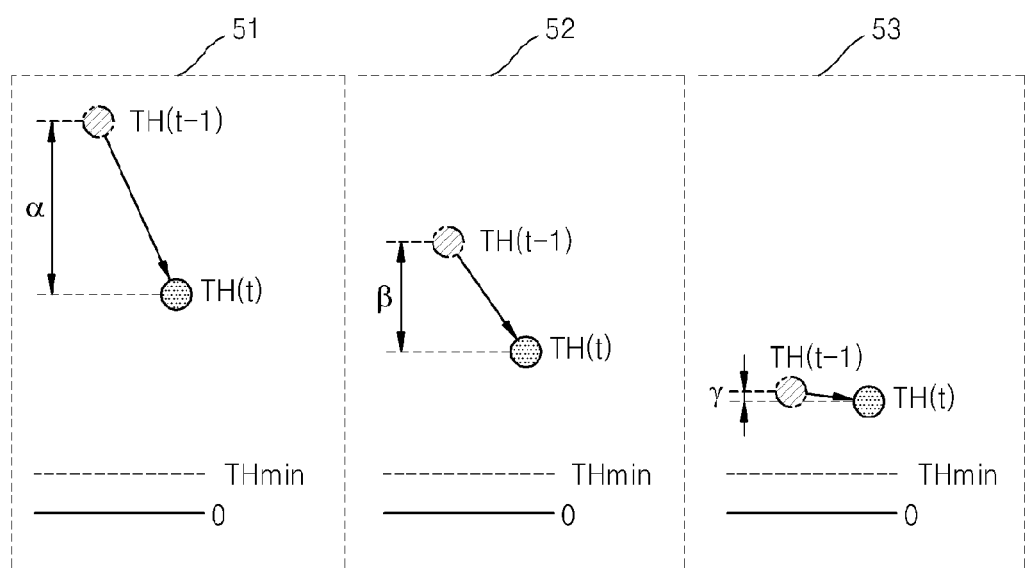
FIG. 5 illustrates an example in which a threshold is reduced by control performed by a proportion controlling unit illustrated in FIG. 2.

FIG. 5 illustrates an example in which a threshold is reduced by control performed by the proportion controlling unit 232 illustrated in FIG. 2. In FIG. 5, a value TH(t−1) is either a first threshold or a feature value of physiological signals selected by the selector 231, and TH(t) is a second threshold updated as the threshold is reduced by control performed by the proportion controlling unit 232. In graphs 51, 52, and 53, the proportion controlling unit 232 updates the value selected by the selector 231 to the second threshold by subtracting a value obtained by applying a predetermined weight to a difference between the value selected by the selector 231 and a minimum threshold $TH_{min}$ from the selected value by performing an arithmetic operation according to Equation 1 discussed above. As can be seen from graphs 51, 52, and 53, the amount $\alpha$, $\beta$, and $\gamma$ by which the value TH(t−1) is reduced to obtain the second threshold TH(t) decreases as the value TH(t−1) approaches the minimum threshold $TH_{min}$.

By performing such an arithmetic operation and control of the proportion controlling unit 232, the variable threshold has a value that is always larger than the minimum threshold, and as updating of the variable threshold is repeated, the variable threshold gradually converges to the minimum threshold. The minimum threshold may be variable as described above.

Figure 6A:
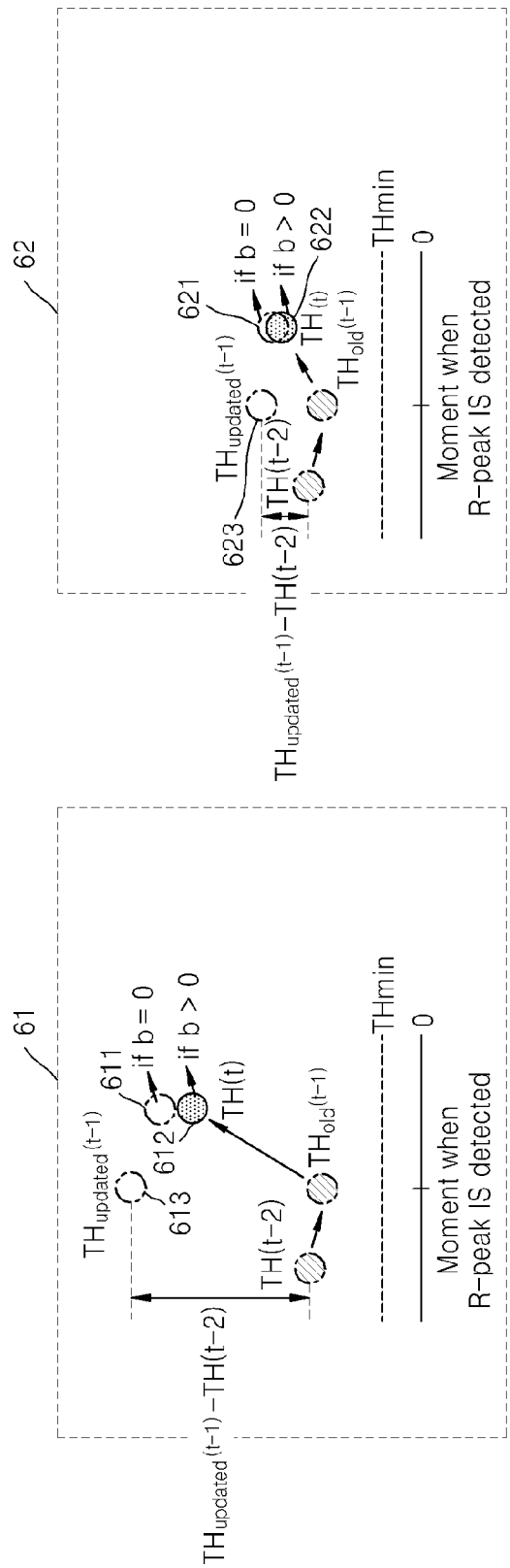
FIG. 6A illustrates an example in which a threshold is reduced by control performed by the proportion controlling unit and a differential controlling unit illustrated in FIG. 2 when an R-peak is detected.

FIG. 6A illustrates an example in which a threshold is reduced by control performed by the proportion controlling unit 232 and the differential controlling unit 233 illustrated in FIG. 2 when an R-peak is detected. In FIG. 6A, $TH_{updated}$(t−1) is a feature value of the peak of the physiological signals selected by the selector 231 when the R-peak is detected, $TH_{old}$(t−1) is a first threshold, TH(t−2) is a previous threshold that was updated to obtain the first threshold $TH_{old}$(t−1), and TH(t) is a second threshold obtained by the proportion controlling unit 232 and the differential controlling unit 233 by updating the feature value $TH_{updated}$(t−1)

In each of graphs 61 and 62, an R-peak is detected, and feature values $TH_{updated}$(t−1) 613 and 623 of the peaks of the physiological signals selected by the selector 231 of FIG. 2 are reduced by control performed by the proportion controlling unit 232 and the differential controlling unit 233 of FIG. 2. The proportion controlling unit 232 reduces the feature $TH_{updated}$(t−1) 613 and 623 to obtain thresholds 611 and 621 (corresponding to a condition in which b=0 in Equation 4 discussed above), and the differential controlling unit 233 further reduces the thresholds 611 and 621 obtained by the proportion controlling unit 232 to update the thresholds 611 and 621 to obtain second thresholds TH(t) 612 and 622 (corresponding to a condition in which b>0 in Equation 4 discussed above).

In detail, referring to Equation 4 discussed above, the differential controlling unit 233 further reduces the thresholds 611 and 621 obtained by the proportion controlling unit 232 by values obtained by applying a predetermined weight b to values obtained by subtracting the previous thresholds TH(t−2) from the feature values $TH_{updated}$(t−1) 613 and 623 selected by the selector 231 to obtain the second thresholds TH(t) 612 and 622.

In graphs 61 and 62, when the R-peak of ECG signals is detected and a value of the R-peak is selected by the selector 231 as new thresholds 613 and 623, the new thresholds 613 and 623 are reduced by the proportion controlling unit 232 and the differential controlling unit 233. The increase in the new threshold 613 in graph 61 is greater than the increase in the new threshold 623 in graph 62, so the differential controlling unit 233 reduces the threshold 611 in graph 61 obtained by the proportion controlling unit 232 by a greater amount than the differential controlling unit 233 reduces the threshold 621 in graph 62 obtained by the proportion controlling unit 232. That is, the differential controlling unit 233 prevents the threshold from increasing too rapidly.

Figure 6B:
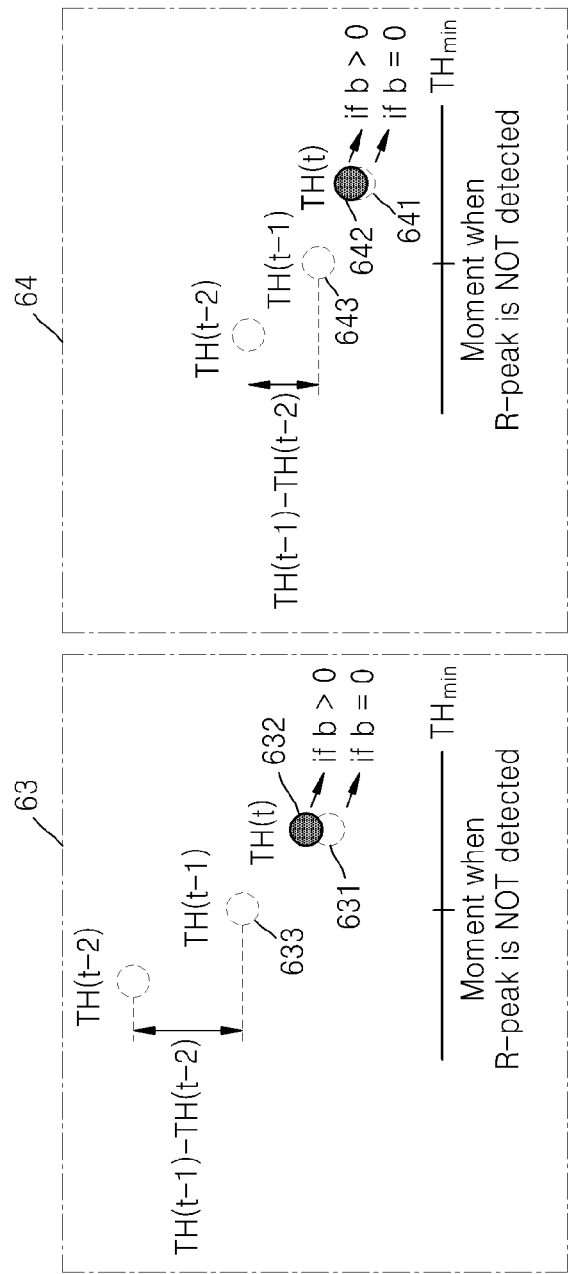
FIG. 6B illustrates an example in which a threshold is reduced by control performed by the proportion controlling unit 232 and the differential controlling unit of FIG. 2 when an R-peak is not detected.

FIG. 6B illustrates an example in which a threshold is reduced by control performed by the proportion controlling unit 232 and the differential controlling unit 233 of FIG. 2 when an R-peak is not detected. In FIG. 6B, TH(t−1) is a first threshold, TH(t−2) is a previous threshold that was updated to obtain the first threshold TH(t−1), and TH(t) is a second threshold obtained by the proportion controlling unit 232 and the differential controlling unit 233 by updating the first threshold TH(t−1).

In each of graphs 63 and 64, when an R-peak is not detected, and thresholds TH(t−1) 633 and 643 selected by the selector 231 of FIG. 2 are reduced by control performed by the proportion controlling unit 232 and the differential controlling unit 233 of FIG. 2. The proportion controlling unit 232 reduces the thresholds 633 and 643 TH(t−1) to obtain thresholds 631 and 641 (corresponding to a condition in which b=0 in Equation 4 discussed above), and the differential controlling unit 233 increases the thresholds 631 and 641 obtained by the proportion controlling unit 232 to update the thresholds 631 and 641 to obtain second thresholds TH(t) 632 and 642 (corresponding to a condition in which b>0 in Equation 4 discussed above).

Thus, graphs 63 and 64 show that when an R-peak is not detected, the differential controlling unit 233 increases the thresholds 631 and 641 obtained by the proportion controlling unit 232 when the proportion controlling unit reduced the first thresholds 633 and 643, while graphs 61 and 62 show that when an R-peak is detected, the differential controlling unit 233 reduces the thresholds 611 and 621 obtained by the proportion controlling unit 232 when the proportion controlling unit 232 reduced the feature values 613 and 623.

In detail, referring to Equation 4 discussed above, the differential controlling unit 233 increase the thresholds 631 and 641 obtained by the proportion controlling unit 232 by values obtained by applying a predetermined weight b to values obtained by subtracting the previous thresholds TH(t−2) from the first thresholds TH(t−1) selected by the selector 231 to obtain the second thresholds TH(t) 632 and 642.

As can be seen from FIG. 6B, when an R-peak is not detected, the first threshold TH(t−1) has a smaller value than the previous threshold TH(t−2). Thus, the value obtained by subtracting the previous threshold TH(t−2) from the first threshold TH(t−1) and the value obtained by applying the predetermined weight b to the resulting value are negative numbers (it is assumed that the predetermined weight b is a positive number). Thus, the differential controlling unit 233 increases the thresholds 631 and 641 obtained by the proportion controlling unit 232 to obtain the second thresholds 632 and 642 as updated thresholds.

That is, compared to FIG. 6A where the differential controlling unit 233 increases the thresholds 611 and 621 obtained by the proportion controlling unit 232 to obtain the second thresholds 612 and 622 that are lower than the thresholds 611 and 621, in FIG. 6B, the differential controlling unit 233 increases the thresholds 631 and 641 obtained by the proportion controlling unit 232 to obtain the second thresholds 632 and 642 that are higher than the thresholds 631 and 641. That is, the differential controlling unit 233 prevents the thresholds from varying rapidly due to the control performed by the proportion controlling unit 232.

In graphs 63 and 64, when the R-peak of ECG signals is not detected, the thresholds 633 and 643 selected by the selector 231 are reduced by the proportion controlling unit 232 to obtain the thresholds 631 and 641, and the thresholds 631 and 641 obtained by the proportion controlling unit 232 are increased by the differential controlling unit 233. Since the proportion controlling unit 232 decreases the first threshold 633 to obtain the threshold 631 by a greater amount in graph 63 than the proportion controlling unit 232 decreases the first threshold 643 to obtain the threshold 641 in graph 64, the differential controlling unit 233 increases the threshold 631 to obtain the second threshold 632 by a greater amount in graph 63 than the differential controlling unit 233 increases the threshold 641 to obtain the second threshold 642 in graph 64. That is, the differential controlling unit 233 increases the thresholds 631 and 632 in proportion to a degree by which the proportion controlling unit 232 reduced the first thresholds 633 and 643, thereby preventing the thresholds from being rapidly decreased.

Although not shown, in another example, the threshold controlling unit 130 of FIG. 2 may further include an update determining unit for determining a method of updating thresholds.

For example, if a sampling rate for obtaining signals is 250 Hz, the update determining unit (not shown) updates thresholds by operating the controlling unit 230 for every sample (at intervals of 4 ms), causing the controlling unit 230 perform multiplication 500 times per second as a result of performing the arithmetic operation of Equation 4, which requires two multiplications each time the arithmetic operation is performed. However, in order to overcome a limitation caused by a performance of the controlling unit 230 or to solve a problem relating to power consumption, the update determining unit (not shown) may reduce the number of arithmetic operations by reducing a frequency of updating thresholds of the controlling unit 230.

For example, when the sampling rate for obtaining physiological signals is 250 Hz, if the update determining unit (not shown) only operates the controlling unit 230 after 50 physiological signals have been obtained, the controlling unit 230 only performs multiplication ten times per second so that power consumption is reduced. The update determining unit (not shown) may determine when a threshold is to be updated by the controlling unit 230 by counting the number of samples of the physiological signals obtained by the signal obtaining unit 210 and operating the controlling unit 230 to update the threshold when a predetermined number of samples have been obtained.

In addition, in another example, the threshold controlling unit 130 of FIG. 2 may further include a linear interpolation unit (not shown). When the threshold is not updated by the controlling unit 230 based on a determination by the update determining unit (not shown), the linear interpolation unit (not shown) may update the threshold by performing linear interpolation.

In detail, in order to provide an effect of updating the threshold similar to operating the controlling unit 230 for each sample, the linear interpolation unit may update the threshold by performing linear interpolation according to the following Equation 5:

$$TH(t+k) = TH(t) - \frac{k}{K+1}(TH(t) - TH_{est}(t+K)) \qquad (5)$$

In Equation 5, K is a predetermined number of samples that are to be obtained before the controlling unit 230 is operated, and t+k is an index of physiological signals to be compared with a threshold. For example, when the update determining unit (not shown) operates the controlling unit 230 after every 50 samples, K is 50, and k is between 1 and 50. Linear interpolation is a process of determining values between two points linearly. In Equation 5, the two points are TH(t) and $TH_{est}$(t+K). Relative to t+k, TH(t) is a previous threshold and thus is currently known, while $TH_{est}$(t+K) is a future threshold and thus is not currently known. However, $TH_{est}$(t+K) may be calculated according to the following Equation 6:

$$TH_{est}(t + K) = TH(t) - a(TH(t) - TH_{min}) - b(TH(t) - TH(t - K)) \qquad (6)$$

Equation 6 is similar in form to Equation 4, and estimates a threshold for a K-th sample. The meaning of Equation 6 will be understood by one of ordinary skill in the art from the discussion of similar Equation 4 above.

Figure 7:
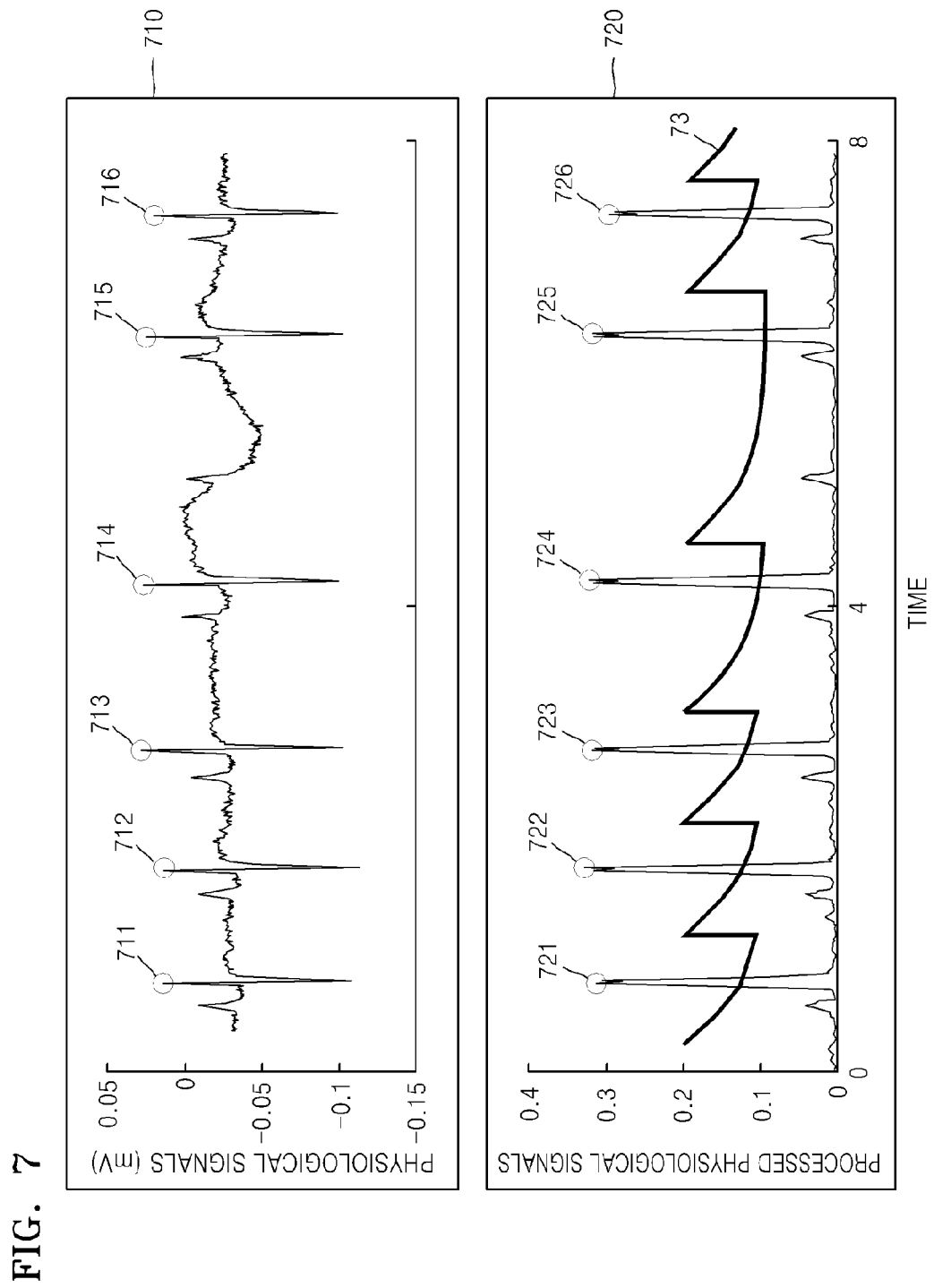
FIG. 7 illustrates an example in which peaks of ECG signals having an irregular interval between the peaks are detected by controlling a variable threshold using the apparatus for detecting physiological signals illustrated in FIG. 1.

FIG. 7 illustrates an example in which peaks of ECG signals having an irregular interval between the peaks are detected by controlling a variable threshold using the apparatus 100 for detecting physiological signals of FIG. 1. Referring to FIG. 7, graph 710 shows physiological signals that have not been processed by the processing unit 120, and graph 720 shows physiological signals that have been processed by the processing unit 120, and also shows a variable threshold 73 for detecting an R-waveform of the physiological signals.

In detail, graph 720 shows physiological signals that have been processed by the processing unit 120 by applying a differentiator and a low-pass filter, for example, an absolute moving average filter, to the physiological signals, and also shows the variable threshold 73 for detecting the R-waveform of the physiological signals that is controlled by the threshold controlling unit 130 of FIG. 2.

Referring to FIG. 7, peaks 711 to 716 of the physiological signals correspond to peaks of R-waveforms of the physiological signals. The processing unit 120 processes the physiological signals, and peaks 721 to 726 of the processed physiological signals correspond to the peaks of the R-waveforms of the physiological signals.

Referring to graph 720 of FIG. 7, the variable threshold 73 increases whenever the peaks 721 to 726 are detected, and then gradually decreases until the next peak is detected. However, even though the variable threshold 73 gradually decreases for a relatively long time after the peak 724 is detected because a time interval from a time when the peak 724 is detected to a time when the peak 725 is detected is relatively long compared to time intervals between times the other peaks are detected in graph 720, the variable threshold 73 does not converge to 0, but converges to a minimum threshold as a result of the control performed by the proportion controlling unit 232.

This is because the threshold controlling unit 130 reduces the variable threshold based on a minimum threshold, and controls the variable threshold to always be higher than the minimum threshold. Since values other than a peak to be detected do not exceed the minimum threshold, the determining unit 220 does not recognize a value other than the peak to be detected as a peak. That is, even when an interval between peaks to be detected is irregular, the determining unit 220 is able to accurately recognize peaks.

Figure 8:
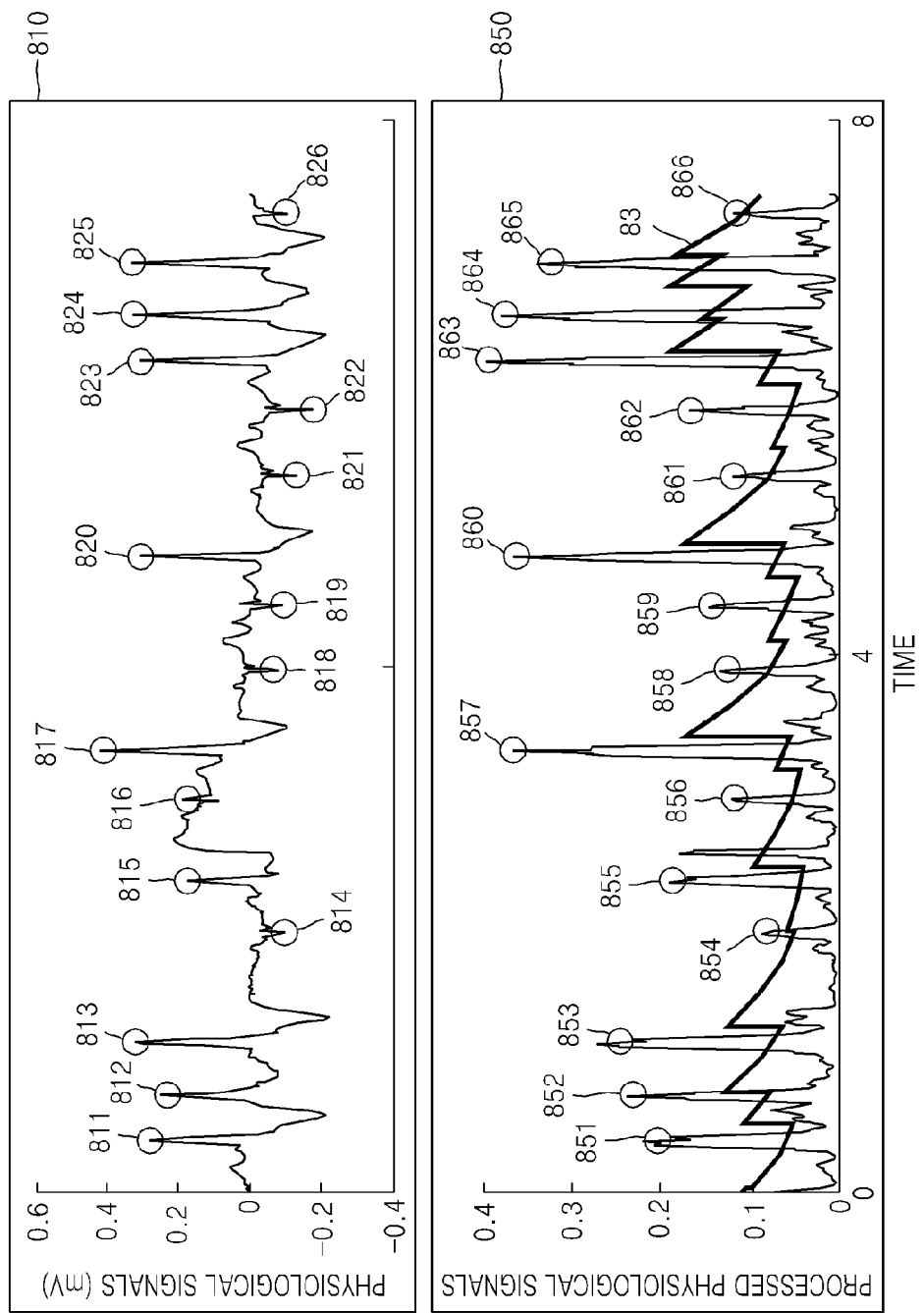
FIG. 8 illustrates an example in which peaks of ECG signals having different peak values are detected by controlling a variable threshold using the apparatus for detecting physiological signals illustrated in FIG. 1.

FIG. 8 illustrates an example in which peaks of ECG signals having different peak values are detected by controlling a variable threshold using the apparatus 100 for detecting physiological signals of FIG. 1. Referring to FIG. 8, graph 810 shows physiological signals that have not been processed by the processing unit 120, and graph 820 shows physiological signals that have been processed by the processing unit 120, and also shows a variable threshold 83 for detecting an R-waveform of the physiological signals.

In detail, graph 820 shows physiological signals that have been processed by the processing unit 120 by applying a differentiator and a low-pass filter, for example, an absolute moving average filter, to the physiological signals, and also shows the variable threshold 83 for detecting the R-waveform of the physiological signals that is controlled by the threshold controlling unit 130 of FIG. 2.

Referring to FIG. 8, peaks 811 to 826 of the physiological signals correspond to peaks of R-waveforms of the physiological signals. The processing unit 120 processes the physiological signals, and peaks 851 to 866 of the processed physiological signals correspond to the peaks of the R-waveforms of the physiological signals.

Referring to graph 820 of FIG. 8, the variable threshold 83 increases whenever the peaks 851 to 866 are detected, and then gradually decreases until the next peak is detected. However, feature values of the peaks 851 to 866 are greatly different from each other, and a variation pattern of the variable threshold 83 is not relatively uniform compared to the variable threshold 73 of FIG. 7.

Nevertheless, the differential controlling unit 233 prevents the variable threshold 83 from varying rapidly. Thus, even when a peak having a relatively large feature value is detected, the variable threshold 83 is not rapidly increased. Thus, the determining unit 220 may detect the next peak even if the next peak has a relatively small feature value by using the variable threshold 83.

Figure 9:
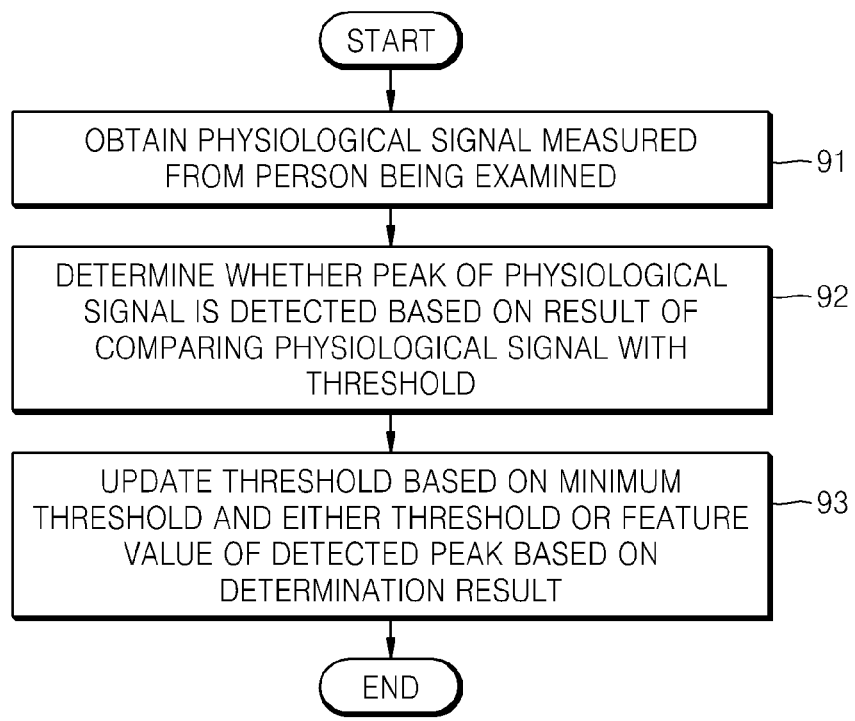
FIG. 9 is a flowchart illustrating an example of a method of controlling a threshold for detecting peaks of physiological signals.

FIG. 9 is a flowchart illustrating an example of a method of controlling a threshold for detecting peaks of physiological signals. Referring to FIG. 9, the method of controlling a threshold includes operations to be performed by the threshold controlling unit 130 illustrated in FIGS. 1 and 2. Thus, although omitted here for conciseness, the description of the threshold controlling unit 130 is also applicable to the method of controlling a threshold illustrated in FIG. 9.

In operation 91, the signal obtaining unit 210 obtains a physiological signal measured from a person being examined.

In operation 92, the determining unit 220 determines whether a peak of the physiological signal is detected based on a result of comparing the physiological signal obtained by the signal obtaining unit 210 with a threshold. For example, the peak of the physiological signal may be a peak of an R-waveform of an ECG signal.

In operation 93, the controlling unit 230 updates the threshold based on a minimum threshold and either the threshold or a feature value of the detected peak based on a determination result obtained by the determining unit 220. For example, when the determination result obtained by the determining unit 220 is that a peak is detected, the controlling unit 230 selects the feature value of the detected peak, and when the determination result obtained by the determining unit 220 is that a peak is not detected, the controlling unit 230 selects the threshold. The controlling unit 230 updates the threshold by reducing the selected value by a value obtained by applying a predetermined weight to a difference between the selected value and the minimum threshold.

As described above, when a threshold for detecting peaks of physiological signals, such as ECG signals, is variably controlled, even when an interval between the peaks is irregular or a difference between peak values is large, the peaks can be accurately detected.

In addition, in a conventional method of controlling a threshold, in the related art, a predetermined weight is applied to reduce a variable threshold without considering a minimum threshold. Thus, the conventional method is not suitable for detecting fluctuating physiological signals having diverse values. On the other hand, in the above-described examples, a variable threshold is controlled based on a minimum threshold, and accordingly a fluctuating waveform having diverse values can be detected. In addition, in the above-described examples, the variable threshold is controlled based on the amount of variation of the variable threshold so that a fluctuating waveform having diverse values can be detected.

The processing unit 120, the threshold controlling unit 130, the determining unit 131, the controlling unit 132, the signal obtaining unit 133, the signal obtaining unit 210, the determining unit 220, the controlling unit 230, the selector 231, the proportion controlling unit 232, the differential controlling unit 233, the update determining unit, and the linear interpolation unit described above may be implemented using one or more hardware components, one or more software components, or a combination of one or more hardware components and one or more software components.

A hardware component may be, for example, a physical device that physically performs one or more operations, but is not limited thereto. Examples of hardware components include amplifiers, differential amplifiers, operational amplifiers, low-pass filters, high-pass filters, band-pass filters, analog-to-digital converters, digital-to-analog converters, registers, differentiators, comparators, arithmetic units, functional units, memory devices, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for controlling a threshold for detecting peaks of physiological signals, the apparatus comprising:
    electrodes configured to electrically contract a user to be examined to measure a physiological signal from the user to be examined;
    a memory configured to store the physiological signal and a detection threshold; and
    a processor configured to:
        obtain the physiological signal,
        determine whether the physiological signal exceeds the detection threshold which, when exceeded, indicates a peak of the physiological signal has been detected,
        update, in response to the processor determining the physiological signal exceeds the detection threshold, the detection threshold by calculating a difference between a predetermined minimum threshold value of the detection threshold and a feature value of the detected peak and a difference between a previous detection threshold and the feature value of the detected peak, and
        update, in response to the processor determining the physiological signal does not exceed the detection threshold, the detection threshold by calculating a difference between the predetermined minimum threshold value of the detection threshold and the detection threshold and a difference between the previous detection threshold and the detection threshold,
    wherein the processor is further configured to control a speed, at which the updated detection threshold is reduced, according to the calculated difference and a weight adjusted based on a user environment, and
    wherein the previous detection threshold was updated to obtain the detection threshold.

2. The apparatus of claim 1, wherein the minimum threshold value of the detection threshold is a value to which the detection threshold converges as the detection threshold is updated by the processor.

3. The apparatus of claim 1, wherein the minimum threshold value of the detection threshold varies in real time based on the feature value of the detected peak.

4. The apparatus of claim 1, wherein the processor is further configured to update the detection threshold based on the feature value of the detected peak and a value obtained by applying a predetermined weight to a difference between the feature value of the detected peak and the minimum threshold value of the detection threshold when the result obtained by the processor is that a peak of the physiological signal is detected.

5. The apparatus of claim 1, wherein the processor is further configured to control the detection threshold based on the detection threshold and a value obtained by applying a predetermined weight to the difference between the detection threshold and the minimum threshold value of the detection threshold when the result obtained by the processor is that a peak of the physiological signal is not detected.

6. The apparatus of claim 1, wherein the processor is further configured to update the detection threshold based on the detection threshold and the previous detection threshold that was updated to obtain the detection threshold.

7. The apparatus of claim 1, wherein the processor is further configured to update the detection threshold based on a value obtained by applying a predetermined weight to the difference between the feature value of the detected peak and the previous detection threshold that was updated to obtain the detection threshold when the result obtained by the processor is that a peak of the physiological signal is detected.

8. The apparatus of claim 1, wherein the processor is further configured to control the detection threshold based on a value obtained by applying a predetermined weight to the difference between the detection threshold and the previous detection threshold that was updated to obtain the detection threshold when the result obtained by the processor is that a peak of the physiological signal is not detected.

9. An apparatus for detecting physiological signals, the apparatus comprising:
    electrodes configured to be attached to a user to be examined to measure a physiological signal from the user to be examined;
    a memory configured to store the measured physiological signal and a detection threshold; and
    a processor configured to:
        process the measured physiological signal using a predetermined processing method to obtain a processed physiological signal,
        determine whether the processed physiological signal exceeds the detection threshold which, when exceeded, indicates a peak of the physiological signal has been detected,
        update, in response to the processor determining the physiological signal exceeds the detection threshold, the detection threshold by calculating a difference between a predetermined minimum threshold value of the detection threshold and a feature value of the detected peak and a difference between a previous detection threshold and the feature value of the detected peak, and
        update, in response to the processor determining the physiological signal does not exceed the detection threshold, the detection threshold by calculating a difference between the predetermined minimum threshold value of the detection threshold and the detection threshold and a difference between the previous detection threshold and the detection threshold, wherein the processor is further configured to control a speed, at which the updated detection threshold is reduced, according to the calculated difference and a weight adjusted based on a user environment, and wherein the previous detection threshold was updated to obtain the detection threshold.

\* \* \* \* \*